US010676560B2

(12) United States Patent
Padsalgikar

(10) Patent No.: US 10,676,560 B2
(45) Date of Patent: Jun. 9, 2020

(54) BIOSTABLE POLYURETHANES

(71) Applicant: Aortech International plc, Glasgow (GB)

(72) Inventor: Ajay D. Padsalgikar, Plymouth, MN (US)

(73) Assignee: Aortech International plc, Glasgow (GB)

( * ) Notice: Subject to any disclaimer, the term of this patent is extended or adjusted under 35 U.S.C. 154(b) by 71 days.

(21) Appl. No.: 15/995,050

(22) Filed: May 31, 2018

(65) Prior Publication Data

US 2018/0298139 A1 Oct. 18, 2018

Related U.S. Application Data

(63) Continuation of application No. 15/368,300, filed on Dec. 2, 2016, now Pat. No. 9,994,668, which is a continuation of application No. 14/852,251, filed on Sep. 11, 2015, now Pat. No. 9,512,261, which is a continuation of application No. 14/216,190, filed on Mar. 17, 2014, now Pat. No. 9,175,130, which is a continuation of application No. 12/225,753, filed as application No. PCT/AU2007/000409 on Mar. 29, 2007, now Pat. No. 8,674,035.

(60) Provisional application No. 60/744,097, filed on Mar. 31, 2006.

(30) Foreign Application Priority Data

Mar. 31, 2006 (AU) ................. 2006901675

(51) Int. Cl.

| C08G 77/04 | (2006.01) |
|---|---|
| C08G 18/61 | (2006.01) |
| A61L 27/18 | (2006.01) |
| A61L 27/50 | (2006.01) |
| C08G 18/10 | (2006.01) |
| C08G 18/40 | (2006.01) |
| C08G 18/48 | (2006.01) |
| C08G 18/32 | (2006.01) |
| C08G 18/76 | (2006.01) |
| C08G 18/66 | (2006.01) |
| A61L 29/06 | (2006.01) |
| A61L 31/06 | (2006.01) |
| C08G 18/44 | (2006.01) |

(52) U.S. Cl.
CPC ............ C08G 18/61 (2013.01); A61L 27/18 (2013.01); A61L 27/50 (2013.01); A61L 29/06 (2013.01); A61L 31/06 (2013.01); C08G 18/10 (2013.01); C08G 18/3206 (2013.01); C08G 18/3228 (2013.01); C08G 18/4009 (2013.01); C08G 18/44 (2013.01); C08G 18/48 (2013.01); C08G 18/4858 (2013.01); C08G

18/6607 (2013.01); C08G 18/7671 (2013.01); C08G 18/7685 (2013.01)

(58) Field of Classification Search
CPC ........ C08G 77/16; C08G 18/61; C08G 18/48; C08G 18/7671
See application file for complete search history.

(56) References Cited

U.S. PATENT DOCUMENTS

| 4,528,343 | A | 7/1985 | Kira |
|---|---|---|---|
| 6,395,265 | B1 | 5/2002 | Mougin et al. |
| 6,420,452 | B1 | 7/2002 | Gunatillake et al. |
| 6,841,646 | B2 | 1/2005 | Yang et al. |
| 6,858,680 | B2 | 2/2005 | Gunatillake et al. |
| 6,915,158 | B2 | 7/2005 | Björling |
| 6,915,168 | B1 | 7/2005 | Benz et al. |
| 8,207,245 | B2 | 6/2012 | Padsalgikar et al. |
| 8,674,035 | B2 | 3/2014 | Padsalgikar |
| 9,175,130 | B2 | 11/2015 | Padsalgikar |
| 9,512,261 | B2 | 12/2016 | Padsalgikar et al. |
| 9,994,668 | B2 | 6/2018 | Padsalgikar |
| 2002/0028901 | A1 | 3/2002 | Gunatillake et al. |
| 2005/0060028 | A1* | 3/2005 | Horres ............ A61L 31/10 623/1.38 |
| 2007/0162103 | A1 | 7/2007 | Case et al. |
| 2009/0118455 | A1 | 5/2009 | Gunatillake et al. |
| 2009/0182111 | A1 | 7/2009 | Padsalgikar |
| 2014/0343243 | A1 | 11/2014 | Padsalgikar |
| 2016/0096913 | A1 | 4/2016 | Padsalgikar |
| 2017/0210844 | A1 | 7/2017 | Padsalgikar |

FOREIGN PATENT DOCUMENTS

| AU | 2007233559 B2 | 7/2008 |
|---|---|---|
| JP | 60-238315 | 11/1985 |
| JP | 60238315 A | 11/1985 |
| JP | 63154722 A | 6/1988 |

(Continued)

OTHER PUBLICATIONS

Chun (Polymer International, 27 (1992) 177-185).*
"U.S. Appl. No. 12/225,753 , Response filed Sep. 27, 2013 to Non Final Office Action dated Sep. 19, 2013", 7 pgs.
"U.S. Appl. No. 12/225,753, Advisory Action dated Aug. 22, 2013", 2 pgs.
"U.S. Appl. No. 12/225,753, Final Office Action dated Jun. 13, 2013", 7 pgs.
"U.S. Appl. No. 12/225,753, Final Office Action dated Sep. 12, 2011", 8 pgs.
"U.S. Appl. No. 12/225,753, Non Final Office Action dated Mar. 1, 2013", 7 pgs.
"U.S. Appl. No. 12/225,753, Non Final Office Action dated Mar. 3, 2011", 8 pgs.

(Continued)

Primary Examiner — Kuo Liang Peng
(74) Attorney, Agent, or Firm — Schwegman Lundberg & Woessner, P.A.

(57) ABSTRACT

The present invention relates to a biostable polyurethane or polyurea comprising: (a) a soft segment comprising a polysiloxane of the general formula (I); and (b) greater than 0 and less than 40 wt % of a hard segment which is a reaction product of a diisocyanate and a linear difunctional chain extender, processes for their preparation and their use in the manufacture of biomaterials, devices, articles or implants.

10 Claims, 5 Drawing Sheets

(56) References Cited

FOREIGN PATENT DOCUMENTS

| JP | 02135210 A | 5/1990 |
|---|---|---|
| JP | 10509742 A | 9/1998 |
| JP | 2001500912 A | 1/2001 |
| JP | 2002543231 A | 12/2002 |
| JP | 2003505562 A | 2/2003 |
| JP | 2005270268 A | 10/2005 |
| JP | 2007077359 A | 3/2007 |
| JP | 2008073877 A | 4/2008 |
| JP | 2008514314 A | 5/2008 |
| JP | 2009531474 A | 9/2009 |
| JP | 2010509742 A | 3/2010 |
| WO | WO-9813405 A1 | 4/1998 |
| WO | WO-1998013405 A1 | 4/1998 |
| WO | WO-1998050086 A2 | 11/1998 |
| WO | WO-9903863 A1 | 1/1999 |
| WO | WO-1999003863 A1 | 1/1999 |
| WO | WO-0064971 A1 | 11/2000 |
| WO | WO-0107499 A1 | 2/2001 |
| WO | WO-2004029123 A1 | 4/2004 |
| WO | WO-2005052019 A1 | 6/2005 |

OTHER PUBLICATIONS

"U.S. Appl. No. 12/225,753, Non Final Office Action dated Sep. 19, 2013", 8 pgs.
"U.S. Appl. No. 12/225,753, Notice of Allowance dated Oct. 28, 2013", 10 pgs.
"U.S. Appl. No. 12/225,753, Response filed Mar. 6, 2012 to Final Office Action dated Sep. 12, 2011", 9 pgs.
"U.S. Appl. No. 12/225,753, Response filed May 14, 2013 to Non Final Office Action dated Mar. 1, 2013", 11 pgs.
"U.S. Appl. No. 12/225,753, Response filed Jun. 21, 2011 to Non Final Office Action dated Mar. 3, 2011", 12 pgs.
"U.S. Appl. No. 12/225,753, Response filed Aug. 13, 2013 to Final Office Action dated Jun. 13, 2013", 10 pgs.
"U.S. Appl. No. 14/216,190, Corrected Notice of Allowance dated Aug. 14, 2015", 6 pgs.
"U.S. Appl. No. 14/216,190, Non Final Office Action dated Oct. 6, 2014", 7 pgs.
"U.S. Appl. No. 14/216,190, Notice of Allowance dated May 29, 2015", 9 pgs.
"U.S. Appl. No. 14/216,190, Response filed Apr. 6, 2015 to Non Final Office Action dated Oct. 6, 2014", 8 pgs.
"U.S. Appl. No. 14/852,251, Non Final Office Action dated Apr. 22, 2016", 7 pgs.
"U.S. Appl. No. 14/852,251, Notice of Allowance dated Aug. 5, 2016", 8 pgs.
"U.S. Appl. No. 14/852,251, Preliminary Amendment filed Dec. 15, 2015", 7 pgs.
"U.S. Appl. No. 15/368,300, Notice of Allowance dated Feb. 8, 2018", 9 pgs.
"U.S. Appl. No. 15/368,300, Notice of Allowance dated Jun. 5, 2017", 10 pgs.
"U.S. Appl. No. 15/368,300, Preliminary Amendment filed Apr. 13, 2017", 6 pgs.
"U.S. Appl. No. 15/368,300, Preliminary Amendment filed Dec. 2, 2016", 3 pgs.
"U.S. Appl. No. 14/852,251, Response filed Jun. 6, 2016 to Non-Final Office Action dated Apr. 22, 2016", 8 pgs.
"Australian Application Serial No. 2006901675, International Search Report dated May 15, 2006", 3 pgs.
"Australian Application Serial No. 2007233559, Notice of Acceptance dated Apr. 7, 2008", 3 pgs.
"Australian Application Serial No. 2007233559, Notice of Allowance of Amendments dated Nov. 8, 2011", 1 pg.
"Australian Application Serial No. 2007233559, Office Action dated Feb. 27, 2008", 3 pgs.
"Australian Application Serial No. 2007233559, Office Action dated Mar. 28, 2008", 1.
"Australian Application Serial No. 2007233559, Office Action dated Jun. 22, 2011", 1 pg.
"Australian Application Serial No. 2007233559, Office Action dated Oct. 17, 2011", 1 pg.
"Australian Application Serial No. 2007233559, Response filed Mar. 17, 2008 to Office Action dated Feb. 27, 2008", 4 pgs.
"Australian Application Serial No. 2007233559, Response filed Apr. 2, 2008 to Office Action dated Mar. 28, 2008", 2 pgs.
"Australian Application Serial No. 2007233559, Response filed Nov. 3, 2011 to Office Action dated Oct. 17, 2011", 1 pg.
"Australian Application Serial No. 2007233559, Voluntary Amendment filed Jun. 17, 2011", 2 pgs.
"European Application Serial No. 07718656.7, Office Action dated Apr. 12, 2013", 13 pgs.
"European Application Serial No. 07718656.7, Office Action dated May 31, 2012", 3 pgs.
"European Application Serial No. 07718656.7, Response filed Mar. 1, 2012 to Office Action dated Aug. 22, 2011", 6 pgs.
"European Application Serial No. 07718656.7, Response filed Dec. 10, 2012 to Office Action dated May 31, 2012", 31 pgs.
"European Application Serial No. 07718656.7, Supplementary EP Search Report dated Aug. 3, 2011", 13 pgs.
"European Application Serial No. 07718656.7, Supplementary European Search Report dated Aug. 3, 2011", 4 pgs.
"International Application Serial No. PCT/AU2007/000409, International Preliminary Report on Patentability dated Jan. 2, 2008", 11 pgs.
"International Application Serial No. PCT/AU2007/000409, International Search Report dated Jun. 11, 2007", 3 pgs.
"International Application Serial No. PCT/AU2007/000409, International Search Report dated Jun. 11, 2007", 4 pgs.
"International Application Serial No. PCT/AU2007/000409, International Written Opinion dated Jun. 11, 2007", 4 pgs.
"Japanese Application Serial No. 2009-501784, Amendment filed Mar. 29, 2010", with English translation of claims, 35 pgs.
"Japanese Application Serial No. 2009-501784, Examiners Decision of Final Refusal dated May 13, 2014", (w/ English Translation), 4 pgs.
"Japanese Application Serial No. 2009-501784, Office Action dated Jan. 8, 2013", (w/ English Translation), 8 pgs.
"Japanese Application Serial No. 2009-501784, Response filed Jul. 3, 2013 to Office Action dated Jan. 8, 2013", w/English claims, 11 pgs.
"Polymer Preprints", vol. 54, No. 1, (2005), 387-388.
Adhikari, Raju, et al., "The Effect of Diisocyanate Isomer Composition on Properties and Morphology of Polyurethanes Based on 4,4'-Dicyclohexyl Methane Diisocyanate and Mixed Macrodiols (PDMS-PHMO)", Journal of Applied Polymer Science, vol. 73, (1999), 573-582.
Chun, Y.-C., et al., "Synthesis and Characterization of Poly(Siloxane-Urethane)s", Polymer International, 27, (1992), 177-185.
Goto, A., et al., "Germanium- and Tin-Catalyzed Living Radical Polymerizations of Styrene", Polymer Preprints, 46(2), (2005), 245-246.
Gunatillake, Pathiraja, et al., "Poly(dimethylsiloxane)/Poly(hexamethylene oxide) Mixed Macrodiol Based Polyurethane Elastomers. I. Synthesis and Properties", Journal of Applied Polymer Science, vol. 76, (2000), 2026-2040.
Hassan, C. M, et al., "Cellular PVA Hydrogels Produced by Freeze/Thawing", Journal of Applied Polymer Science, vol. 76, (2000), 2075-2079.
Kim, Y. S., et al., "Synthesis and Characterization of Segmented Polyurethanes and Their Blends With Thermally Conductive Aluminium Nitride", Polymer Preprints, 42(2), (2001), 695-696.
Kuo, P.-L., et al., "Preparation and Ionic Conductivity of Solid Polymer Electrolytes Based on Segmented Polysiloxane-Modified Polyurethane", Macromolecular Chemistry and Physics, 203, (2002), 230-237.
Martin, D. J., et al., "Polydimethylsiloxane/polyether-mixed macrodiol-based polyurethane elastomers: biostability", Biomaterials, 21, (2000), 1021-1029.

(56) References Cited

OTHER PUBLICATIONS

Wang, F., et al., "Synthesis and Characterization of Poly(dimethyl siloxane) Modified Polyurethane", Polymer Preprints, 38(1), (1997), 308-309.

Yuan, M., et al., "Polymerization of Lactides and Lactones. III. Ring-Opening Polymerization of DL-Lactide by the (n3-C3H5)2Sm(u2-Cl)2(u3-Cl)2Mg(tmed)(u2-Cl)Mg(tmed)Complex", Journal of Applied Polymer Science, 73, (1999), 2857-2862.

* cited by examiner

BIOSTABLE POLYURETHANES

This application is a continuation application of U.S. patent application Ser. No. 15/368,300, filed Dec. 2, 2016, which is a continuation application of U.S. patent application Ser. No. 14/852,251, filed Sep. 11, 2015, now U.S. Pat. No. 9,512,261, issued on Dec. 6, 2016, which is a continuation application of U.S. patent application Ser. No. 14/216,190, filed Mar. 17, 2014, now U.S. Pat. No. 9,175,130, issued on Nov. 3, 2015, which is a continuation application of U.S. patent application Ser. No. 12/225,753, filed Apr. 1, 2009, now U.S. Pat. No. 8,674,035, issued on Mar. 18, 2014, which application is a nationalization under 35 U.S.C. 371 of PCT/AU2007/000409, filed Mar. 29, 2007 and published as WO 2007/112485 A1, on Oct. 11, 2007, which claims priority under 35 U.S.C. 119 to Australian Application No. 2006901675, filed Mar. 31, 2006; and which claims priority under 35 U.S.C. 119(e) to U.S. Provisional Patent Application Ser. No. 60/744,097, filed Mar. 31, 2006; which applications and publication are incorporated herein by reference and made a part hereof in their entirety.

The present invention relates to polyurethanes and processes for their preparation. The polyurethanes are biostable, creep resistant, acid resistant and abrasion resistant which makes them useful in the manufacture of biomaterials and medical devices, articles or implants, in particular long term implantable medical devices in the fields of cardiology, orthopaedics, plastic surgery and gastroenterology.

BACKGROUND

The development of methodology to incorporate high silicone loadings in the soft segment of polyurethanes has resulted in the production of biostable polyurethanes (Elast-Eon™). The soft segment of these polyurethanes is based on 80 wt % of a hydroxyl terminated polydimethylsiloxane (PDMS) and 20 wt % of a polyether polyol specifically polyhexamethylene oxide (PHMO).

It was thought that the presence of the polyether was necessary in order to act as a compatibiliser between thermodynamically diverse molecules of the isocyanate rich hard segment and the silicone rich soft segment. Polyurethanes with silicone contents higher than 80 wt % of the soft segment resulted in poorer mechanical properties which at that time seemed to corroborate the compatibiliser theory.

The technology of Elast-Eon production has more recently evolved leading to significant process breakthroughs that allow the incorporation of higher silicone content into the soft segment without a corresponding decrease in mechanical properties.

A considerable amount of work has also been done in understanding the biologically induced degradation mechanisms in polyurethanes. Oxidising radicals emanating from foreign body giant cells (FBGC) in the vicinity of the implant are seen to be the major source of degradation of polyurethane based medical devices. As a result, it has been shown that the presence of oxidisable groups in polyurethanes are the primary sites of the initiation of degradation. Therefore, a reduction in the content of groups prone to oxidation will lead to an increase in the biological stability of the polyurethanes. As a consequence, it is now desirable to have a soft segment which is based on PDMS instead of PDMS in combination with a polyether polyol.

SUMMARY

According to the present invention there is provided a biostable polyurethane comprising:

(a) a soft segment comprising greater than 98 wt % of a polysiloxane having a molecular weight in the range of 500 to 1500 of the general formula (I)

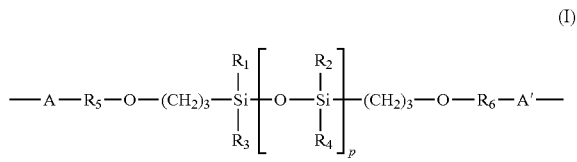

in which
A and A' are O;
$R_1$, $R_2$ $R_3$ and $R_4$ are independently selected from $C_{1-6}$ alkyl;
$R_5$ and $R_6$ are independently selected from $C_{1-12}$ alkylene; and
p is an integer of 1 or greater, preferably 5 to 30, more preferably 8 to 20; and (b) greater than 0 and less than 40 wt % of a hard segment which is a reaction product of a diisocyanate and a linear difunctional chain extender.

The present invention also provides a process for preparing the biostable polyurethane defined above which comprises the steps of:

(i) reacting a hydroxy terminated polysiloxane of formula (I) as defined above with a diisocyanate to form a prepolymer; and
(ii) high shear mixing the prepolymer of step (i) with a linear difunctional chain extender.

Despite having a lower hard segment concentration, the polyurethanes of the present invention surprisingly possess an equivalent tensile modulus to the Elast-Eon polyurethanes in the range of 10 to 55 MPa. This is also accompanied by biological stability and a 10 to 20% improvement in creep resistance, acid resistance and abrasion resistance. These properties make the polyurethanes useful in the manufacture of biomaterials and medical devices, articles or implants.

Thus, the present invention further provides a biomaterial, device, article or implant which is wholly or partly composed of the biostable polyurethanes or polyurethane ureas as defined above.

BRIEF DESCRIPTION OF THE DRAWINGS

In the Examples, reference will be made to the accompanying drawings in which.

DETAILED DESCRIPTION

Figure 1:
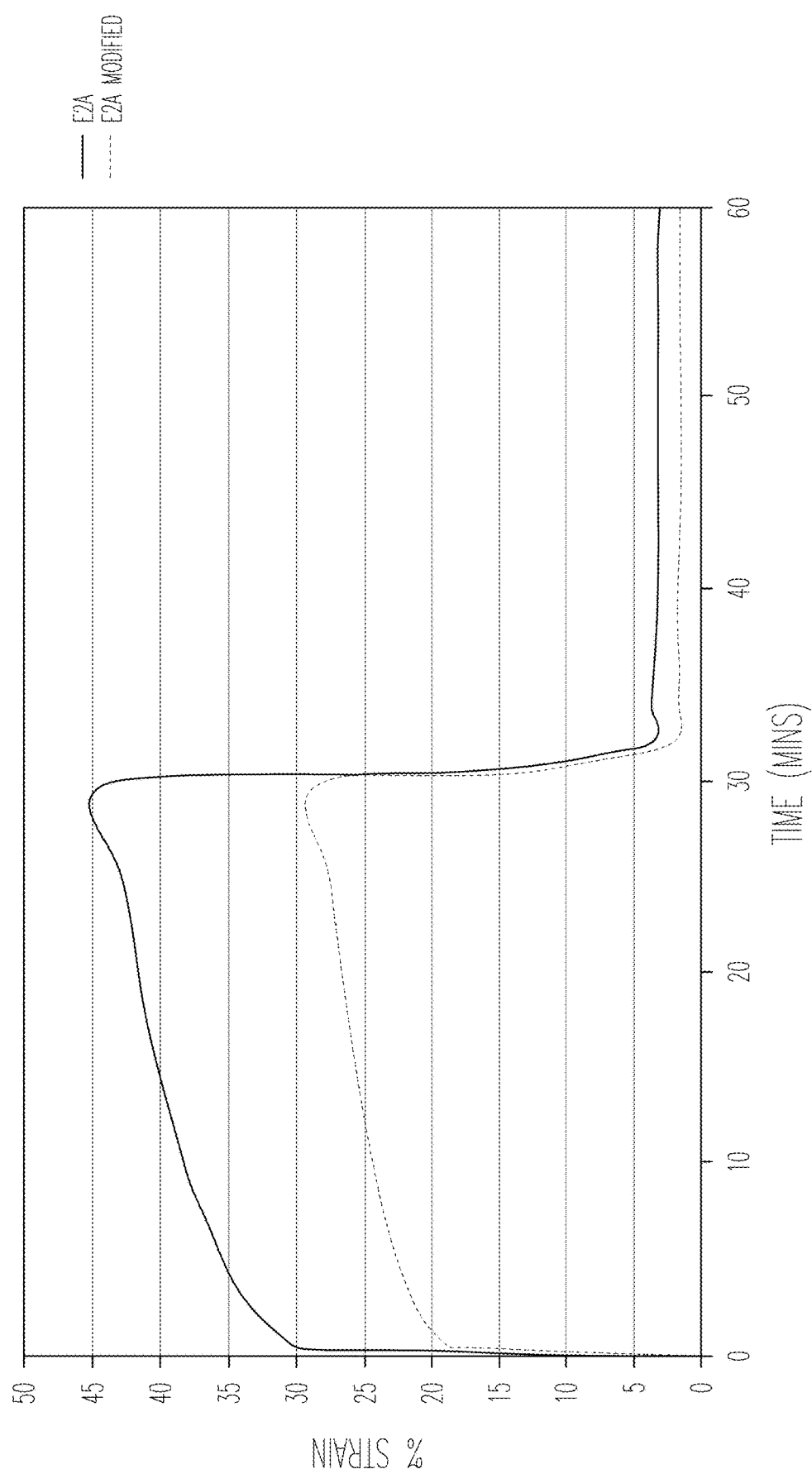
FIG. 1 is a graph showing a comparison of the tensile and recovery (5 MPa loading) between E2A and E2A modified.

The biostable polyurethanes of the present invention possess (a) a soft segment which comprises the polysiloxane of formula (I) defined above and (b) a hard segment which is the reaction product of a diisocyanate and a linear difunctional chain-extender. While in a preferred embodiment the soft segment only comprises the polysiloxane of formula (I), it will be appreciated that other soft segment components such as polyether polyols or polycarbonate polyols may be present in an amount of up to 2 wt %, preferably up to 1 wt % based on the total amount of soft segment.

Suitable polyether polyols include those of formula (II):

HO—[$(CH_2)_m$—O]$_n$—H     (II)

in which
m is an integer of 2 or more, preferably 4 to 18; and
n is an integer of 2 to 50.

Polyether polyols of formula (II) wherein m is 4 or higher such polytetramethylene oxide (PTMO), polyhexamethylene oxide (PHMO), polyheptamethylene oxide, polyoctamethylene oxide (POMO) and polydecamethylene oxide (PDMO) are preferred. The molecular weight range of the polyether polyol is preferably in the range of 200 to 5000, more preferably 200 to 1200.

Suitable polycarbonate polyols include poly(alkylene carbonates) such as poly(hexamethylene carbonate) and poly(decamethylene carbonate); polycarbonates prepared by reacting alkylene carbonate with alkanendiol for example 1,4-butanediol, 1,10-decanediol (DD), 1,6-hexanediol (HD) and/or 2,2-diethyl 1,3-propanediol (DEPD); and silicon based polycarbonates prepared by reacting alkylene carbonate with 1,3-bis(4-hydroxybutyl)-1,1,3,3-tetramethlyldisiloxane (BHTD) and/or alkanediols.

The soft and hard segments of polyurethanes typically phase separate and form separate domains. The hard segments organise to form ordered (crystalline) domains while the soft segments remain largely as amorphous domains and the two in combination are responsible for the excellent mechanical properties of polyurethanes.

The amount of hard segment present in the polyurethanes of the present invention is greater than 0 and less than 40 wt %, preferably in the range of 10 to 39 wt %, more preferably between 25 to 37.5 wt %.

It is surprising that the tensile modulus of the polyurethanes of the present invention decreases as the amount of hard segment decreases.

It is observed that the tensile properties do not seem to be affected significantly by the exclusion of the polyether from the soft segment. In particular, the tensile modulus actually shows an increase even with lower amounts of hard segment concentration. This is clearly a result of enhanced phase separation that occurs with the polyurethanes of the present invention as opposed to the Elast-Eon polyurethanes. The enhanced phase separation also shows up in improvements of properties of creep resistance, abrasion resistance and fatigue resistance.

A significant aspect of the exclusion of the polyether is the resulting improvement in the oxidation resistance of the material. This is measured by subjecting the polyurethanes to a fixed time period test (28-72 days) in an oxidative solution containing high concentration of oxidative radicals such as peroxides. The polyurethanes after the test are examined by various techniques including scanning electron microscopy (SEM) to assess and quantify the level of degradation. These tests are a good indicator of long term biological stability. Polyurethanes containing 100% polysiloxane in the soft segment show remarkable improvements in oxidative stability.

Similar improvements are noted in the resistance to acid degradation with the 100% polysiloxane soft segment polyurethanes showing considerable improvement over the Elast-Eon polyurethanes having a polysiloxane polyether soft segment.

The amount of soft segment present in the polyurethane is at least 60 wt %, more preferably in the range of 60 wt % to 90 wt %, most preferably 60 wt % to 75 wt %.

The high Si content results in polyurethanes which are biostable and show improvements in mechanical properties and acid and abrasion resistance.

The NCO/OH or NRH ratio of the components of the polyurethanes are preferably in the range of 0.97 to 1.03, more preferably 0.985 to 1.015.

Polysiloxane

The polysiloxane is of formula (I) defined above.

The term "$C_{1-6}$ alkyl" as used in formula (I) refers to straight chain, branched chain or cyclic hydrocarbon groups having from 1 to 6 carbon atoms, preferably 1 to 4 carbon atoms, more preferably methyl. Examples include alkyl groups such as methyl, ethyl, propyl, isopropyl, butyl, isobutyl, sec-butyl, tert-butyl, pentyl, neopentyl, hexyl, cyclopropyl, cyclobutyl, cyclopentyl and cyclohexyl.

The term "$C_{1-12}$ alkylene" refers to divalent straight chain, branched chain or cyclic hydrocarbon groups having from 1 to 12 carbon atoms, preferably 1 to 6 carbon atoms, more preferably 1 to 4 carbon atoms. Examples include ethylene, propylene, butylene, pentylene, hexylene, heptalene and octylene, dodecylene, cyclopropylene, cyclopentylene and cyclohexylene.

Preferred polysiloxanes are polysiloxane macrodiols which are hydroxy terminated polysiloxanes of formula (I).

A preferred polysiloxane is PDMS which is a polysiloxane of formula (I) wherein $R_1$ to $R_4$ are methyl and $R_5$ and $R_6$ are as defined above, preferably $C_{1-4}$ alkylene, more preferably ethylene or propylene.

The polysiloxane macrodiols may be prepared according to known procedures or obtained as commercially available products such as X-22-160AS from Shin Etsu in Japan which is a hydroxy terminated polysiloxane of formula (I) in which $R_1$ to $R_4$ are methyl, $R_5$ and $R_6$ are ethylene, X is O and p is 8 to 20.

Other polysiloxanes are polysiloxane macrodiamines which are NHR terminated polysiloxanes of formula (I) in which R is as defined above, for example, amine terminated PDMS in which R is hydrogen, $R_1$ to $R_4$ are methyl and $R_5$ and $R_6$ are as defined above, preferably $C_{1-6}$ alkylene, more preferably ethylene or propylene.

The molecular weight range of the polysiloxane is 500 to 1500.

It will be understood that the molecular weight values referred to herein are "number average molecular weights".

The presence of an ether group increases the polarity of the polysiloxane of formula (I) making it more amenable for reaction with the diisocyanate. Polysiloxanes and diisocyanates are extremely incompatible due to a large difference in their polarities. Any attempt to force a polymerisation between a diisocyanate and a silanol usually results in polymers with poor mechanical properties and the need to employ polymerisation conditions involving a solvent. The polarity of the polysiloxane of formula (I) assists in overcoming any premature phase separation and maintaining good mechanical properties.

Diisocyanate

The diisocyanate may be an aliphatic, cyclic or aromatic diisocyanates such as, for example 4,4'-diphenylmethane diisocyanate (MDI), methylene biscyclohexyl diisocyanate ($H_{12}$MDI), p-phenylene diisocyanate (p-PDI), trans-cyclohexane-1,4-diisocyanate (CHDI), 1,6-diisocyanatohexane (DICH), 1,5-diisocyanaton-aphthalene (NDI), para-tetramethylxylenediisocyanate (p-TMXDI), meta-tetramethylxylene diisocyanate (m-TMXDI), 2,4-toluene diisocyanate (2,4-TDI) isomers or mixtures thereof or isophorone diisocyanate (IPDI). Aromatic diisocyanates such as MDI are preferred due their propensity to form uniform hard blocks that contribute both to good mechanical properties as well as biostability.

The amount of diisocyanate present is preferably in the range of 8 wt % to 35 wt %, more preferably 20 wt % to 35 wt % based on the total weight of the polyurethane.

Chain Extender

The term "difunctional linear chain extender" in the present context means any chain extender having two functional groups per molecule such as diols or diamines which are capable of reacting with an isocyanate group. The functional group is attached to a primary functional carbon atom as opposed to a secondary functional carbon atom in the case of a branched chain extender.

The chain extender generally has a molecular weight range of 500 or less, preferably 15 to 500, more preferably 60 to 450.

The chain extender may be selected from diol or diamine chain extenders.

Examples of diol chain extenders include $C_{1-12}$ alkane diols such as 1,4-butanediol (BDO), 1,6-hexanediol, 1,8-octanediol, 1,9-nonanediol, 1,10-decanediol and 1,12-dodecanediol; cyclic diols such as 1,4-cyclohexanediol, 1,4-cyclohexanedimethanol, 1,4-bis(2-hydroxyethoxy)benzene and p-xyleneglycol; and silicon-containing diols such as 1,3-bis(4-hydroxybutyl) tetramethyldisiloxane and 1,3-bis(6-hydroxyethoxypropyl) tetramethyldisiloxane. Preferably the diol chain extender is BDO.

Suitable diamine chain extenders include $C_{1-12}$ alkane diamines such as 1,2-ethylenediamine, 1,3-propanediamine, 1,4-butanediamine and 1, 6-hexanediamine; and silicon-containing diamines such as 1,3-bis(3-aminopropyl) tetramethyldisiloxane and 1,3-bis(4-aminobutyl)tetramethyldisiloxane.

It is important that the chain extender be linear as the use of a branched chain extender would disrupt the morphology of the polyurethane and result in poor biostability and reduced mechanical properties.

The amount of chain extender present is preferably in the range of 1 wt % to 5 wt %, more preferably 2 wt % to 5 wt % based on the total weight of the polyurethane.

Process

The polyurethanes of the present invention are prepared by a two-step bulk polymerisation procedure. The polymerisation can be carried out in conventional apparatus or within the confines of a reactive injection moulding or mixing machines.

In the two-step method, a prepolymer having terminally reactive polyisocyanate groups is prepared by reacting a hydroxyl terminated polysiloxane of formula (I) with a diisocyanate. The prepolymer is the high shear mixed with a chain extender using any suitable known apparatus such as a high shear and speed mixer for example a Silverson Mixer. The high shear mixing ensures that the morphology of the polyurethane is controlled so that there is proper distribution of the hard segment in the soft segment and to prevent premature phase separation. It is important to disperse evenly the chain extender into the prepolymer. The high shear mixing ensures even distribution before reaction. The polyurethane may then be cured by pouring the liquid polyurethane into Teflon-coated trays and heated to about 100° C. The cured slabs may then be granulated and melted through an extruder at temperatures of about 200° C. The melted polyurethane can then be passed through a strand die and the strands pelletised.

The process described above does not generally cause premature phase separation and yields polyurethanes that are compositionally homogeneous and transparent having high molecular weights. This process also has the advantage of not requiring the use of any solvent to ensure that the soft and hard segments are compatible during synthesis.

A further advantage of the incorporation of polysiloxane segments is the relative ease of processing of the polyurethane by conventional methods such as reactive injection moulding, rotational moulding, compression moulding and foaming without the need of added processing waxes. If desired, however, conventional polyurethane processing additives such as catalysts for example dibutyl tin dilaurate (DBTDL), stannous oxide (SO), 1,8-diazabicyclo[5,4,0]undec-7-ene (DABU), 1,3-diacetoxy-1,1,3,3-tetrabutyldistannoxane (DTDS), 1,4-diaza-(2,2,2)-bicyclooctane (DABCO), N,N,N',N'-tetramethylbutanediamine (TMBD) and dimethyltin dilaurate (DMTD); antioxidants for example Irganox (Registered Trade Mark); radical inhibitors for example trisnonylphenyl phosphite (TNPP); stabilisers; lubricants for example Irgawax (Registered Trade Mark); dyes; pigments; inorganic and/or organic fillers; and reinforcing materials can be incorporated into the polyurethane during preparation. Such additives are preferably added in step (i) of the process of the present invention.

Medical Applications

The polyurethanes of the present invention are particularly useful in preparing biomaterials and medical devices, articles or implants as a consequence of their biostability, creep resistance, acid resistance and abrasion resistance.

The term "biostable" refers to a stability when in contact with cells and/or bodily fluids of living animals or humans.

The term "biomaterial" refers to a material which is used in situations where it comes into contact with the cells and/or bodily fluids of living animals or humans.

The medical devices, articles or implants may include catheters; stylets; bone suture anchors; vascular, oesophageal and bilial stents; cochlear implants; reconstructive facial surgery; controlled drug release devices; components in key hole surgery; biosensors; membranes for cell encapsulations; medical guidewires; medical guidepins; cannularizations; pacemakers, defibrillators and neurostimulators and their respective electrode leads; ventricular assist devices; orthopaedic joints or parts thereof including spinal discs and small joints; cranioplasty plates; intraoccular lenses; urological stents and other urological devices; stent/graft devices; device joining/extending/repair sleeves; heart valves; vein grafts; vascular access ports; vascular shunts; blood purification devices; casts for broken limbs; vein valve, angioplasty, electrophysiology and cardiac output catheters; plastic surgery implants such as breast implant shells; lapbands; gastric balloons; and tools and accessories for insertion of medical devices, infusion and flow control devices.

It will be appreciated that polyurethanes having properties optimised for use in the construction of various medical devices, articles or implants will also have other non-medical applications. Such applications may include toys and toy components, shape memory films, pipe couplings, electrical connectors, zero-insertion force connectors, Robotics, Aerospace actuators, dynamic displays, flow control devices, sporting goods and components thereof, body-conforming devices, temperature control devices, safety release devices and heat shrink insulation.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

EXAMPLES

The invention will now be described with reference to the following non-limiting examples.

Example 1

This example illustrates the preparation and testing of an Elast-Eon 2A (E2A) formulation with 100% silicone in the soft segment.

Synthesis

PDMS (180.00 g, MW 958.15) was degassed at 80° C. for 24 h under vacuum (0.01 torr), the resultant moisture level was <150 parts per million. Molten MDI (1010.63 g, MW 250.00) was weighed into a three-neck round bottom flask equipped with a mechanical stirrer, dropping funnel and nitrogen inlet. The flask was heated in an oil bath at 70° C. The degassed PDMS (2000 g) was then added through a dropping funnel over a period of 2 hours. The PDMS used in this example has the following formula:

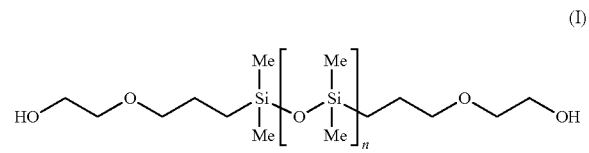

(I)

in which n is 8-20.

After the completion of PDMS addition, the reaction mixture was heated for a further 2 h with stirring under nitrogen at 80° C. The prepolymer mixture was then degassed at 80° C. under vacuum (0.01 torr) for about 1 h. The vacuum was released slowly under nitrogen atmosphere and 2810 g of the degassed prepolymer mixture was weighed into a tall dry polypropylene beaker and immediately placed in a nitrogen circulating oven at 80° C.

BDO (189.3 g, MW 90.00) was previously degassed over 24 h at 60° C. to moisture levels below 50 ppm. The overall stoichiometry was maintained at 1.015. BDO was added into the prepolymer mixture (2810 g) while using a highly dispersive, high shear and high speed mixer such as a Silverson Mixer. The mixture was stirred at high speed (6000 rpm) for about 2 minutes. The polymer mixture was then poured into several Teflon coated moulds and cured to a solid slab for 15 h in a nitrogen circulating oven at 100° C. After full cure the slabs were granulated and extruded in a 25 mm diameter extruder, L/D ratio of 30/1 at a melt temperature of 200° C. The extrudate, in the form of cylindrical rods, was chopped into pellets suitable for further thermoplastic processing.

Tensile Testing

The pellets were compression moulded into 3 mm thick rectangular sheets and samples were cut from these sheets that were subject to various mechanical testing. Table 1 below shows the mechanical data comparison between the two polyurethanes.

TABLE 1

| Material | Si Content % | Soft Segment Composition PDMS/PHMO | Modulus of Elasticity (MPa) | Tensile strength (MPa) | % Strain at break | Tear Strength (kN/m) | Durometer Hardness |
| --- | --- | --- | --- | --- | --- | --- | --- |
| E2A | 48 | 80/20 | 35 | 28 | 500 | 85 | 90A |
| E2A modified | 60 | 100/0 | 56 | 27 | 560 | 84 | 90A |

E2A is made with a soft segment that is a mix of 80 wt % of PDMS 1000 and 20 wt % of PHMO. The ratio of the hard to soft segment in both E2A and the modified version of E2A is 40/60. The hard segment comprises MDI and BDO. The tensile modulus increases with increased PDMS content but all the other properties are comparable.

Creep and Recovery

FIG. 1 is a graph providing a comparison of the tensile creep performance of the polyurethanes. The polyurethanes were loaded to 60N (in about 10 sec), translating to a stress of approximately 5 MPa, and held for 30 minutes. After 30 minutes the polyurethane was taken off the Instron and the gauge length was measured intermittently for 30 minutes.

A surprising improvement in creep and recovery performance is noted in the polyurethane containing 100% silicone in the soft segment.

In-Vitro Accelerated Oxidative Ageing

Using the protocol described in E. M. Christenson, J. M. Anderson, A. Hiltner, Journal of Biomed. Mater. Res. A, 2004, 69, 407 in vitro accelerated aging was performed at 37° C.±1° C. on unstrained film samples in an oxidative solution of 20% hydrogen peroxide in 0.1 M cobalt chloride. The polyurethane films were treated for 24 days with the change of solutions every 3 days in order to maintain a relatively constant concentration of radicals. Film samples were removed every 6 days, washed thoroughly with water, vacuum dried before using for extraction experiments.

Figure 2:
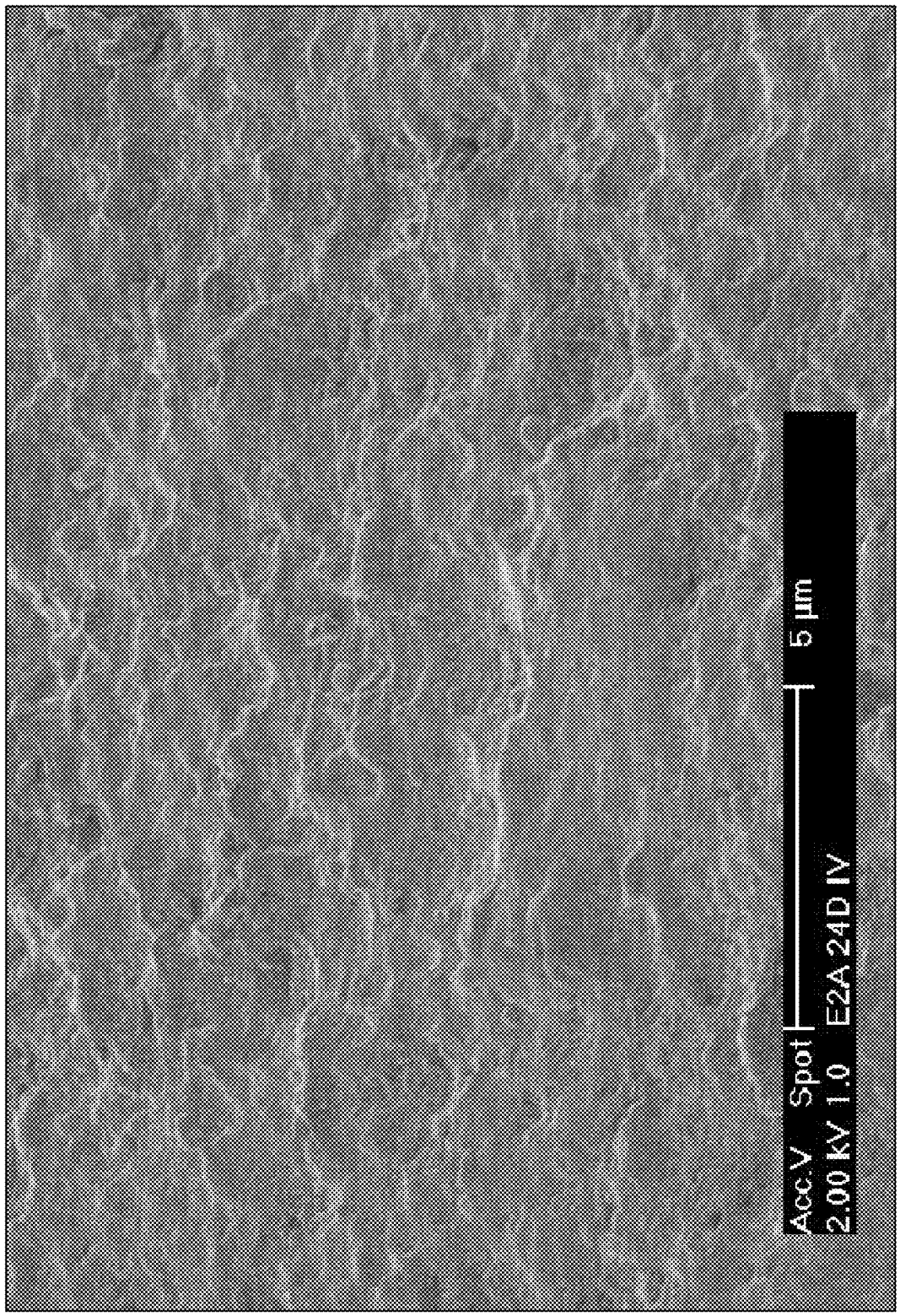
FIG. 2 is a scanning electron micrograph (SEM) at 5000 times magnification for E2A after 24 days in vitro.
Figure 3:
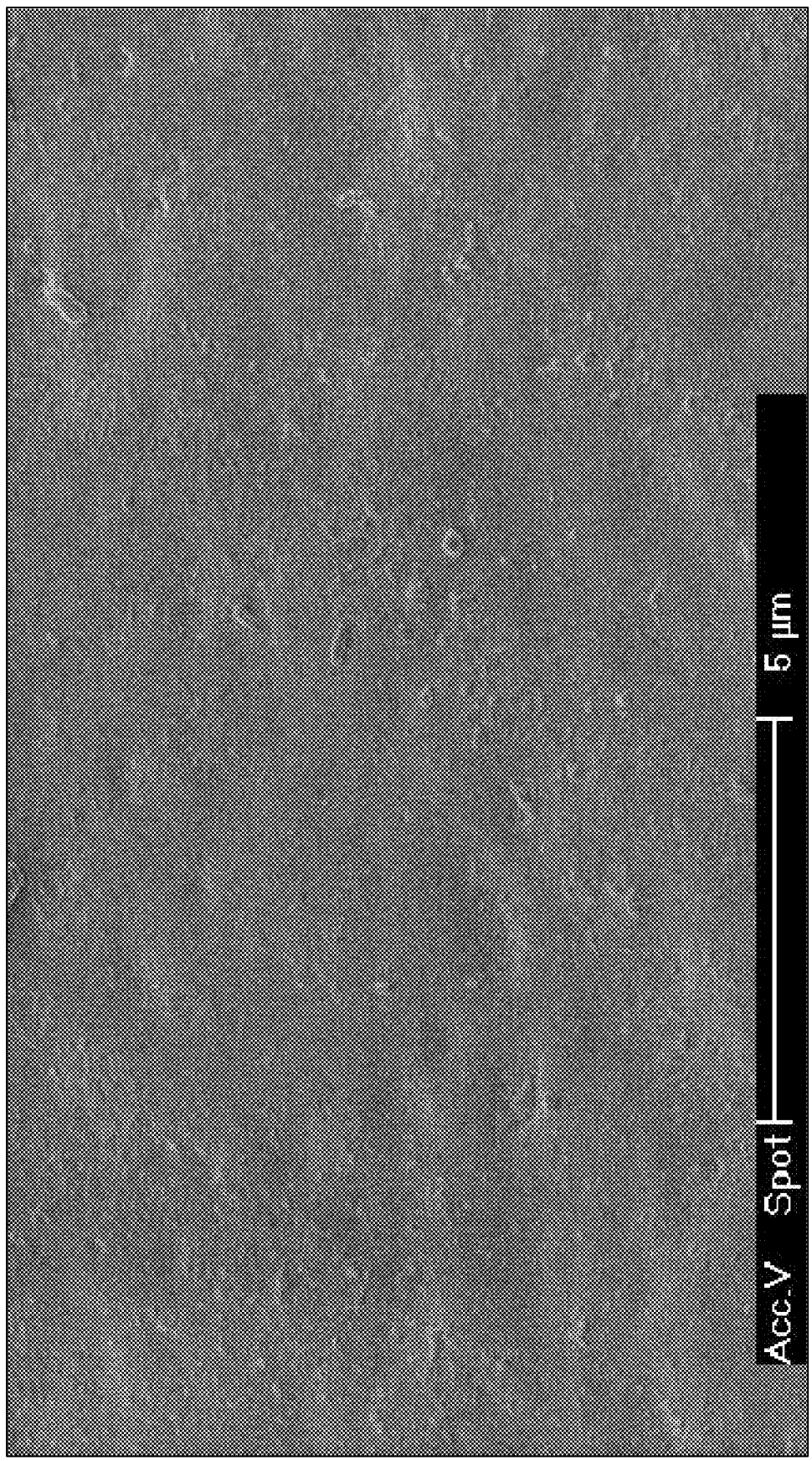
FIG. 3 is a SEM at 5000 times magnification for E2A modified after 24 days in vitro.

The SEMs at 5000 times magnification of the standard and the modified E2A are shown in FIGS. 2 and 3.

From the results it can be seen that the modified E2A performed even better than standard E2A in terms of very low surface degradation. The biological stability that a 100% silicone content E2A provides is superior to the standard E2A.

Example 2

This example illustrates the preparation and testing of E2A formulations with 100% silicone in the soft segment and varying levels of hard segment content.

Synthesis

The synthesis was exactly the same as that used in Example 1, but the levels of the reactants were different as illustrated in Table 2 below.

TABLE 2

| Formulation | Stoichiometry | Hard segment % | MDI (g) | PDMS (g) | BDO (g) |
|---|---|---|---|---|---|
| 1 | 1.015 | 35 | 910.3 | 1950 | 139.7 |
| 2 | 1.015 | 32.5 | 860.14 | 2025 | 114.86 |
| 2 | 1.015 | 30 | 809.97 | 2100 | 90.03 |

These formulations were then compared with equivalent hard block formulations made from a mixed macrodiol (80/20, PDMS/PHMO). The comparative tensile test results set out in Table 3 below.

TABLE 3

| Material | Hard Segment % | Modulus of Elasticity (MPa) | Tensile strength (MPa) | % Strain at break | Tear Strength (kN/m) | Durometer Hardness |
|---|---|---|---|---|---|---|
| Comparative 1 | 35 | 18.6 | 22.5 | 698 | 62.5 | 84A |
| 1 | 35 | 21.0 | 23.1 | 711 | 67.1 | 86A |
| Comparative 2 | 32.5 | 12.7 | 21 | 676 | 56 | 78A |
| 2 | 32.5 | 13 | 22.7 | 675 | 58 | 80A |
| Comparative 3 | 30 | 9.5 | 15.5 | 790 | 48.5 | 76A |
| 3 | 30 | 10.0 | 20.2 | 799 | 52 | 73A |

As can be seen in Table 3, the difference in the tensile modulus decreases as the hard segment % decreases. This result is surprising since the difference in the modulus is high when the hard segment content is 40%, as noted in Example 1. This was probably why the Elast-Eon polyurethanes contain a compatibiliser in conjunction with silicone in order to reduce the stiffness of the polyurethanes. However, the stiffness or modulus difference reduces dramatically as the overall % hard segment of the polyurethanes decreases.

Thus, Elast-Eon of equivalent modulus at lower hard segment concentration can be obtained with a soft segment composed entirely of silicone. This is accompanied by corresponding significant increase in biological stability, creep resistance, acid resistance and abrasion resistance.

Example 3

This example illustrates the characterisation of the E2A and E2A modified materials synthesised in Example 1.

Characterisation Methods

Dynamic Mechanical Analysis.

The dynamic mechanical properties of the copolymers were evaluated using a TA-Q800 DMA and a Gas Cooling Accessory (Model CFL-50) for sub-ambient experiments. Film samples were tested in tension from −120° C. to 150° C. at a heating rate of 3° C./min and frequency of 1 Hz; the static force was preset at 1 N with a force track of 125%.

Small-Angle X-Ray Scattering.

SAXS data were collected on Molecular Metrology SAXS instrument consisting of a three-pinhole collimated camera [using a CuKα radiation source ($\lambda$=0.154 nm)] and a two-dimensional multi-wire detector. The sample-to-detector distance was 1.5 m.

The polyurethane films were cut into 1 cm×1 cm squares, which were stacked to a thickness of approximately 1 mm and secured by tape along the edges. The film stack was supported by placing it between two index cards with a hole for the passage of the x-ray beam. The ensemble was then mounted onto a sample holder provided by Molecular Metrology.

Absolute scattered intensities (in units of $cm^{-1}$) were determined by calibration with a pre-calibrated cross-linked polyethylene (S-2907) secondary standard; this step is essential in order to obtain quantitative details on segment demixing. A silver behenate secondary standard was used to calibrate the scattering vector.

Results

The results, as observed with the characterisation, indicate important behavioural aspects of the material.

Figure 4:
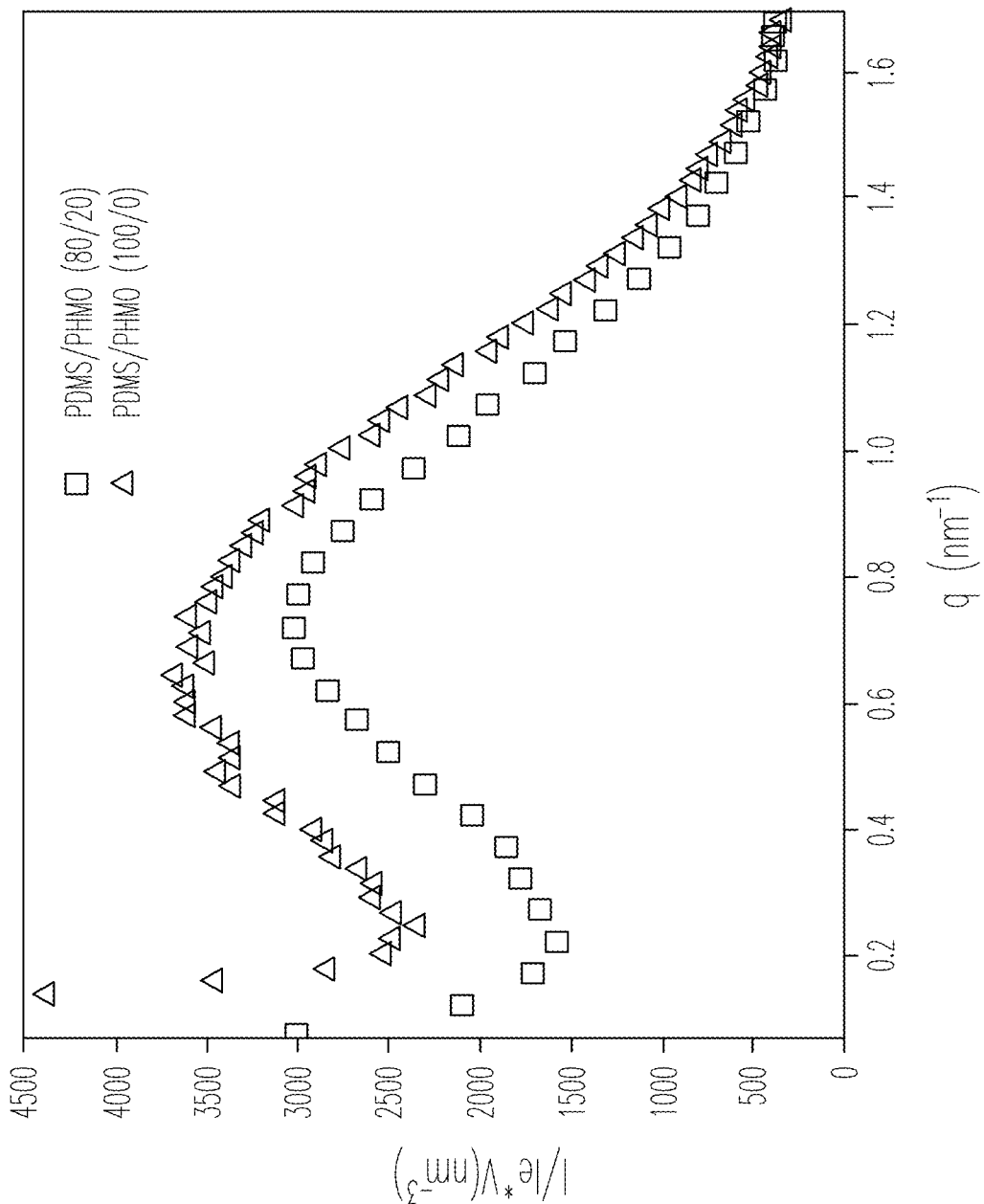
FIG. 4 is a graph showing background corrected SAXS intensities as a function of scattering vector: ■E2A and ▲E2A modified.

The SAXS results in FIG. 4 show that the polyurethane made with only PDMS in the soft segment has a greater degree of phase separation than the polyurethane made with a blend of polyols, PDMS and PHMO. The data are presented as $I/I_e V$, where I is the scattered intensity, $I_e$ the intensity scattered by a single electron under identical conditions, and V the irradiated sample volume. The peak position ($q_{max}$) is indicative of the mean interdomain spacing, d, by $d=2\pi/q_{max}$.

Figure 5:
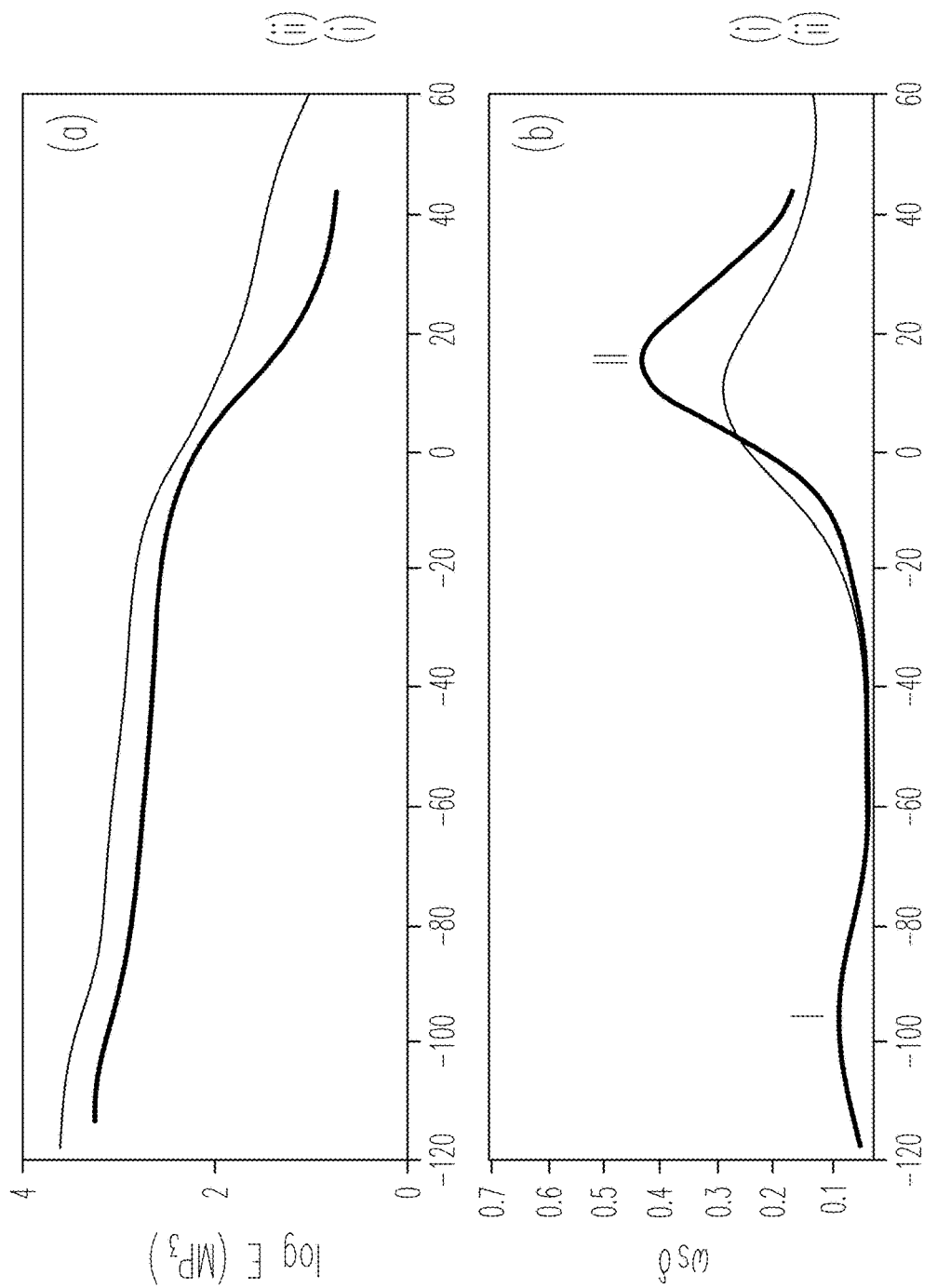
FIG. 5 is a graph showing (a) storage (E') and (b) dissipation factor (tan d) as a function of temperature for Elast-Eon 2A. Untreated material (i) and oxidised sample (ii).

FIG. 5 shows the DMA plot of E2A before and after performing in vitro oxidative ageing. The glass transition temperature of the PDMS phase is ~−120° C. while that of the PHMO phase ~20° C. Upon undergoing oxidation, the PDMS transition is unaffected while the PHMO transition broadens with a decrease in the tan d value and an increase in the storage modulus. This shows that only the PHMO phase is affected on oxidation and is therefore the more susceptible part of the polymer structure in terms of biostability.

It will be understood to persons skilled in the art of the invention that many modifications may be made without departing from the spirit and scope of the invention.

What is claimed is:

1. A biostable polyurethane comprising:
   (a) 60-90 wt-% of a soft segment consisting essentially of a residue derived from 100 wt-% of a polysiloxane having a molecular weight of 500-1500 of the formula:

A-R5-O—$(CH_2)_3$—[Si(R1)(R3)]—[—O—Si(R2)(R4)]$_p$—$(CH_2)_3$—O-R6-A'  (I)

in which
   A and A' are OH;
   R1, R2, R3 and R4 are methyl;
   R5 and R6 are ethylene:
   p is an integer of 1 or greater;

optionally, up to 2% of a polyether polyol of the formula HO—[(CH$_2$)$_m$—O]$_n$—H where m is an integer of 4-18 and n is an integer of 2-50; and (b) 10-40 wt-% of a hard segment which is the reaction product of a diisocyanate and a linear difunctional chain extender.

2. The polyurethane of claim 1, wherein the diisocyanate is 20-35 wt-% based on the total weight of the polyurethane.

3. The polyurethane of claim 2, wherein the chain extender is 2-5 wt-% based on the total weight of the polyurethane.

4. The polyurethane of claim 3, wherein the chain extender is a (C$_1$-C$_{12}$)alkane diol or a (C$_3$-C$_{12}$)alkane diamine.

5. The chain extender of claim 4, wherein the (C$_1$-C$_{12}$) alkane diol is 1,4-butane diol.

6. The polyurethane of claim 2, wherein the diisocyanate is an aromatic diisocyanate.

7. The polyurethane of claim 6 wherein the diisocyanate is 4,4'-diphenylmethyl diisocyanate.

8. A biomaterial, device, article or implant which is wholly or partly composed of the polyurethane of claim 1.

9. A biomaterial, device, article or implant according to claim 8 which is selected from catheters; stylets; bone suture anchors; vascular, oesophageal and bilial stents; cochlear implants; reconstructive facial surgery; controlled drug release devices; components in key hole surgery; biosensors; membranes for cell encapsulations; medical guidewires; medical guidepins; cannularizations; pacemakers, defibrillators and neurostimulators and their respective electrode leads; ventricular assist devices; orthopaedic joints or parts thereof; spinal discs and small joints; cranioplasty plates; intraoccular lenses; urological stents and other urological devices; stent/graft devices; device joining/extending/repair sleeves; heart valves; vein grafts; vascular access ports; vascular shunts; blood purification devices; casts for broken limbs; vein valve, angioplasty, electrophysiology and cardiac output catheters; plastic surgery implants; breast implant shells; lapbands; gastric balloons; tools and accessories for insertion of medical devices, infusion and flow control devices; toys and toy components; shape memory films; pipe couplings; electrical connectors; zero-insertion force connectors; Robotics; Aerospace actuators; dynamic displays; flow control devices; sporting goods and components thereof; body-conforming devices; temperature control devices; safety release devices and heat shrink insulation.

10. The polyurethane of claim 1 which contains up to 2% of the polyether polyol.

* * * * *

UNITED STATES PATENT AND TRADEMARK OFFICE
CERTIFICATE OF CORRECTION

PATENT NO. : 10,676,560 B2
APPLICATION NO. : 15/995050
DATED : June 9, 2020
INVENTOR(S) : Ajay D. Padsalgikar It is certified that error appears in the above-identified patent and that said Letters Patent is hereby corrected as shown below:

In the Claims

Column 12, Line 8, Claim 9, delete "intraoccular" and insert --intraocular-- therefor Signed and Sealed this
Twenty-ninth Day of December, 2020

Andrei Iancu
*Director of the United States Patent and Trademark Office*